United States Patent
Said et al.

(10) Patent No.: US 10,646,425 B1
(45) Date of Patent: May 12, 2020

(54) COSMETIC PRODUCT FOR THE SKIN COMPRISING A COMBINATION OF ACETIC ACID AND NATURAL ESSENTIAL OILS

(71) Applicants: Hayel Said, Simi Valley, CA (US); Bassam Ghanem, Warhanieh (LB); Hussam Ghanem, Warhanieh (LB); Faissal Ghanem, La Crescenta, CA (US)

(72) Inventors: Hayel Said, Simi Valley, CA (US); Bassam Ghanem, Warhanieh (LB); Hussam Ghanem, Warhanieh (LB); Faissal Ghanem, La Crescenta, CA (US)

(73) Assignee: DISTINGUE LLC, Glendale, CA (US)

( * ) Notice: Subject to any disclaimer, the term of this patent is extended or adjusted under 35 U.S.C. 154(b) by 0 days.

(21) Appl. No.: 16/137,437

(22) Filed: Sep. 20, 2018

Related U.S. Application Data

(63) Continuation-in-part of application No. 14/945,534, filed on Nov. 19, 2015, now abandoned.

(60) Provisional application No. 62/082,417, filed on Nov. 20, 2014.

(51) Int. Cl.
| | |
|---|---|
| *A61K 8/36* | (2006.01) |
| *A61K 8/34* | (2006.01) |
| *A61K 8/92* | (2006.01) |
| *A61K 47/44* | (2017.01) |
| *A61K 47/10* | (2017.01) |
| *A61K 31/19* | (2006.01) |
| *A61K 36/73* | (2006.01) |
| *A61Q 19/00* | (2006.01) |
| *A61Q 19/08* | (2006.01) |

(52) U.S. Cl.
CPC ................ *A61K 8/36* (2013.01); *A61K 8/342* (2013.01); *A61K 8/922* (2013.01); *A61K 31/19* (2013.01); *A61K 36/73* (2013.01); *A61K 47/10* (2013.01); *A61K 47/44* (2013.01); *A61Q 19/00* (2013.01); *A61Q 19/08* (2013.01); *A61K 2800/591* (2013.01)

(58) Field of Classification Search
CPC .......... A61K 8/36; A61K 8/342; A61K 8/922; A61K 31/19; A61K 36/73; A61K 47/10; A61K 47/44; A61K 2800/591; A61Q 19/00; A61Q 19/08
USPC .......................................................... 424/401
See application file for complete search history.

(56) References Cited

U.S. PATENT DOCUMENTS

| | | | | |
|---|---|---|---|---|
| 2012/0271251 | A1* | 10/2012 | Webb | A61K 31/19 604/290 |
| 2014/0194482 | A1* | 7/2014 | Farber | A61K 9/0014 514/390 |
| 2016/0158143 | A1* | 6/2016 | Gan | A61K 8/062 424/62 |
| 2017/0027856 | A1* | 2/2017 | Florence | A61K 8/99 |

\* cited by examiner

*Primary Examiner* — Sin J Lee
(74) *Attorney, Agent, or Firm* — White-Welker & Welker, LLC; Matthew T. Welker, Esq.

(57) ABSTRACT

Apple cider vinegar, may be applied in different ways to the skin, the preferred way of application is a cream or a lotion which can be left on the skin for 10-15 minutes or preferably overnight. The objectionable odor of vinegar is masked or eliminated by the inclusion of certain natural essential oils such as lavender oil, rose oil, rosewood oil, geranium oil, tea tree oil, rosemary oil, sandalwood oil, lemongrass oil, violet oil and ginger oil. These natural essential oils also practically eliminate any potential skin irritation that may result from high concentrations of the vinegar.

4 Claims, No Drawings

COSMETIC PRODUCT FOR THE SKIN COMPRISING A COMBINATION OF ACETIC ACID AND NATURAL ESSENTIAL OILS

TECHNICAL FIELD OF THE INVENTION

The present invention relates generally to a cosmetic cream. More specifically, the present invention relates to a topical analgesic for sensitive skin that provides a fast acting and deeply penetrating topical analgesic, which does not irritate sensitive skin.

BACKGROUND OF THE INVENTION

The history of Apple Cider Vinegar can be traced as far back as 3000 B.C. when the father of medicine, Hippocrates, used it on his patients. ACV (Apple Cider Vinegar), or natural, un-distilled Apple Cider Vinegar, was discovered by Hippocrates to be a powerful agent that helps to promote a longer and healthier life.

Apple cider vinegar is a type of vinegar made from cider or apple must and has a pale to medium amber color. Unpasteurized or organic ACV contains mother of vinegar, which has a cobweb-like appearance and can make the vinegar look slightly congealed. It can be produced with different acidity levels, the most commercially available acidity level being 5%.

ACV's legacy describes its mighty body cleansing and weight loss qualities that can be traced back to when it was used in Egyptian urns, as preservatives by the Babylonians, as a disease-fighting agent by Julius Caesar's army, as a flavor additive by the Greeks and Romans, and as a body deodorizer in the middle ages in Paris.

Although ACV is mainly used as a nature-pathic remedy rather than something that a doctor would normally prescribe, ACV has been used all over the world for thousands of years for an abundance of health reasons, however, its use a cosmetic agent for the skin, has not been much documented either in the patent literature or elsewhere.

SUMMARY OF THE INVENTION

Apple cider vinegar, may be applied in different ways to the skin, the preferred way of application is a cream or a lotion which can be left on the skin for 10-15 minutes or preferably overnight. The objectionable odor of vinegar is masked or eliminated by the inclusion of certain natural essential oils such as lavender oil, rose oil, rosewood oil, geranium oil, tea tree oil, rosemary oil, sandalwood oil, lemongrass oil, violet oil and ginger oil. These natural essential oils also practically eliminate or drastically minimize any potential skin irritation that may result from the low pH of the vinegar.

BRIEF DESCRIPTION OF THE DRAWINGS

Not Applicable.

DETAILED DESCRIPTION AND BEST MODE OF THE INVENTION

In the following detailed description of the invention a plurality of exemplary embodiments of the invention are taught. These embodiments are described in sufficient detail to enable those skilled in the art to practice the invention, but other embodiments may be utilized and logical, mechanical, electrical, chemical, and other changes may be made without departing from the scope of the present invention. The following detailed description is therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention.

Composition

The present invention generally is a chemical mixture. Vinegar has been used as a food ingredient for centuries. Its cosmetic use however has been very limited. The Inventors have established a therapeutic use previously unknown for vinegar, and specifically apple cider vinegar, in the treatment of various skin conditions.

The inventors have unexpectedly found that apple cider vinegar with repeated use can effectively treat skin conditions such as acne, eczema, rosacea, insect bites, chapped skin, and can reduce wrinkles and skin blemishes associated with aging and prolonged sun exposure.

Also the inventors have found that the objectionable odor of vinegar can be masked or eliminated by the inclusion of certain natural essential oils such as lavender oil, rose oil, rosewood oil, geranium oil, tea tree oil, rosemary oil, sandalwood oil, lemongrass oil, violet oil and ginger oil. These natural essential oils also practically eliminate or drastically minimize any potential skin irritation that may result from the low pH of the vinegar.

Every person has a protective acid mantle, which is a thin layer of oil, on the outer surface of his/her skin. This protective acid mantle protects the skin and keeps it acidic. Skin is naturally acidic and functions best when it's at a pH of around 5.5.

Each time a person washes their face or applies any cosmetic, skin, or beauty product, they disrupt this natural acid mantle. Under normal circumstances, healthy skin will bounce right back and rebalance on its own quickly. However, when the acid mantle is disturbed, specifically during the time between being disturbed and rebalanced, the skin grows vulnerable to infections and other irritations. Using harsh products, over cleaning, or even the effects of stress can cause the acid mantle to function improperly, throwing the skin's pH out of its desired balance. As a result, many people begin to experience acne and dryness.

Apple cider vinegar (ACV) is produced with different acidity levels. Depending on the acidity level it can have a pH range of about 2.5 to 3. When diluted, ACV assists in bringing the skin's pH back to its normal levels. By restoring the skin's balance, apple cider vinegar helps the skin function optimally, warding off bacteria and shedding dead skin cells at the proper rate so pores are unblocked and skin remains healthy.

Although vinegar, and more specifically apple cider vinegar, may be applied in different ways to the skin, the preferred way of application is a cream or a lotion which can be left on the skin for 10-15 minutes or preferably overnight. An example of such an application vehicle for minor skin conditions stated above is the following formulation. Concentrations are expressed as weight percentages as shown in Table 1.

TABLE 1

| Ingredient | Weight by % of Composition |
| --- | --- |
| Water | 45.8 |
| Apple cider vinegar (5% acidity) | 35.0 |
| Cetearyl Alcohol and Ceteareth-20 | 8.0 |
| Isostearyl alcohol | 2.0 |
| Steareth-2 | 2.0 |
| Steareth-21 | 2.0 |
| Lemongrass oil | 1.8 |
| Lavender oil | 1.0 |
| Rose oil | 1.0 |
| Tea tree oil | 0.5 |
| Geranium oil | 0.5 |
| Fragrance | 0.4 |
| Total: | 100 |

When subjects with light cases of acne, rosacea or eczema used the above formula, applying it twice daily to the affected areas for four weeks, all symptoms disappeared and the skin recovered its normal complexion.

Another formulation for moderate or severe skin conditions stated above is the formula shown in Table 2, which resulted in complete remission of these skin conditions when applied twice a day to the affected areas over a six-week period:

TABLE 2

| Ingredient | Weight by % of Composition |
| --- | --- |
| Apple cider vinegar (5% acidity) | 82.6 |
| Cetearyl Alcohol and Ceteareth-20 | 8.0 |
| Isostearyl alcohol | 2.0 |
| Steareth-2 | 2.0 |
| Steareth-21 | 2.0 |
| Lavender oil | 1.0 |
| Rose oil | 1.0 |
| Geranium oil | 1.0 |
| Fragrance | 0.4 |
| Total: | 100 |

Referring to Table 3, yet another formulation for moderate or severe skin conditions is shown. This formulation is for Rosacea and it also has a specific mixing process for its proper preparation as experimental research has determined that there combination and mixing of ingredients is ineffective in creating the mixture.

The basic and major ingredient is in all formulas and in the same percentage taught by the present invention, essential oils are changing in all formulas and as taught, the essential oils are of minor percentage compared to the major ingredient.

The process for creating the mixture of the third embodiment of the present invention states with Phases A and B being separately heated to 80 C. Phase B is then added to Phase A and mixed together for 15 min at 80 C and a speed of 275 rpm. Phase C is added at 75 C and mixed for 15 min while increasing mixing speed to 500 rpm. Phase D is added at 70 C and mixed for another 15 minutes while cooling down slowly by turning off the heat. Rapid cooling followed and the batch was removed for filling at 45 C into 30 ml bottles.

TABLE 3

RAW MATERIAL

| PHASE | TRADE NAME | INCI NAME | % | 400 Kg |
| --- | --- | --- | --- | --- |
| A | Apple Cider Vinegar (Heinz, 5% acidity) | Acetic Acid | 67.000 | 268.000 |
| | Water | Water | 13.165 | 52.660 |
| | Glycerin | Glycerin | 3.000 | 12.000 |
| B | Emulgade 1000NI (BASF) | Cetearyl Alcohol & Ceteareth-20 | 6.000 | 24.000 |
| | Prisorine ISOH 3515-LQ-(GD) (Croda) | Isostearyl Alcohol | 1.000 | 4.000 |
| | Neobee M-20 (Stepan) | Caprylic/Capric Triglyceride | 2.000 | 8.000 |
| | Cetiol SB 45 (Evonik) | Butyrospermum Parkii (Shea) butter | 1.000 | 4.000 |
| | Brij S2-SO-(AP) (Croda) | Steareth-2 | 0.500 | 2.000 |
| | Lipocol S-21 Vantage) | Steareth-21 | 0.500 | 2.000 |
| C | Simulgel INS 100 (Seppic) | Hydroxyethyl Acrylate/Sodium Acryioyldlmethyl Taurate copolymer & Isohexadecene & Polysorbate 60 | 3.000 | 12.000 |
| D | Lavender oil (Nature's oil, Ohio) | Lavnder oil (Lavandula angustifolia) | 1.800 | 7.200 |
| | Sheer Freesia BBW Fragrance oil (Nature's oil) | Freesia Fragrance Oil (Freesia alba) | 0.200 | 0.800 |
| | Lemongrass oil (Nature's oil, Ohio) | Lemongrass oil (Cymbopogon flexuosus) | 0.200 | 0.800 |
| | Verbena (wild) oil (HBNO) | Verbena oil (Lippia javanica) | 0.010 | 0.040 |
| | Pepermint oil (HBNO) | Peppermint oil (Peppermint Arvensis/Piperita) | 0.025 | 0.100 |
| | Ginger Grass oil (Nature's oil)) | Ginger oil (Zingiber officinalis) | 0.200 | 0.800 |
| | Jojoba oil (Nature;s oil, Ohio) | Jojoba oil (Simmondsia Chinensis) | 0.200 | 0.800 |
| | Vitamin E | Tocopherol Acetate | 0.200 | 0.800 |
| | | | 100.000 | 400.000 |

As to a further discussion of the manner of usage and operation of the present invention, the same should be apparent from the above description. Accordingly, no further discussion relating to the manner of usage and operation will be provided.

It is appreciated that the relationships for the parts of the invention, to include variations, are deemed readily apparent and obvious to one of ordinary skill in the art, and all equivalent relationships in the above description are intended to be encompassed by the present invention.

In addition, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A cosmetic product for the skin, the chemical composition consisting of:
about 67 weight percentage of Acetic Acid of 5% acidity;
about 13 weight percentage of Water;
about 3 weight percentage of Glycerin;

about 6 weight percentage of Cetearyl Alcohol and Ceteareth-20;

about 1 weight percentage of Isostearyl Alcohol;

about 2 weight percentage of Caprylic/Capric Triglyceride;

about 1 weight percentage Butyrospermum Parkii (Shea) butter;

about 0.500 weight percentage of Steareth-2;

about 0.500 weight percentage of Steareth-21;

about 3 weight percentage of Hydroxyethyl Acrylate/Sodium Acryloyldimethyl Taurate copolymer, Isohexadecane and Polysorbate 60;

about 3 weight percentage of essential oils; and about 0.200 weight percentage of Tocopherol Acetate.

2. The cosmetic product of claim 1, wherein the Acetic Acid is apple cider vinegar.

3. The cosmetic product of claim 2, wherein the essential oils are selected from the group consisting of: lavender oil, rose oil, rosewood oil, geranium oil, tea tree oil, rosemary oil, sandalwood oil, lemongrass oil, violet oil and ginger oil.

4. The cosmetic product of claim 2, wherein the essential oils consist of:

about 1.8% Lavender oil (*Lavandula angustifolia*);

about 0.200% Freesia Fragrance Oil (*Freesia alba*);

about 0.200% Lemongrass oil (*Cymbopogon flexuosus*);

about 0.010% Verbena oil (*Lippia javanica*);

about 0.025% Peppermint oil (Peppermint *Arvensis/Piperita*);

about 0.200% Ginger oil (*Zingiber officinalis*); and about 0.200% Jojoba oil (*Simmondsia Chinensis*).

* * * * *